(12) United States Patent
Hong et al.

(10) Patent No.: US 10,337,968 B2
(45) Date of Patent: Jul. 2, 2019

(54) AUTOMATIC REDUCTION APPARATUS FOR PRE-TREATING SAMPLE FOR RADIOCARBON DATING

(71) Applicant: KOREA INSTITUTE OF GEOSCIENCE AND MINERAL RESOURCES, Daejeon (KR)

(72) Inventors: Wan Hong, Daejeon (KR); Jung Hun Park, Daejeon (KR)

(73) Assignee: KOREA INSTITUTE OF GEOSCIENCE AND MINERAL RESOURCES, Yuseong-Gu, Daejeon (KR)

(*) Notice: Subject to any disclaimer, the term of this patent is extended or adjusted under 35 U.S.C. 154(b) by 0 days.

(21) Appl. No.: 14/411,177

(22) PCT Filed: Dec. 3, 2014

(86) PCT No.: PCT/KR2014/011748
§ 371 (c)(1),
(2) Date: Dec. 24, 2014

(87) PCT Pub. No.: WO2015/115728
PCT Pub. Date: Aug. 6, 2015

(65) Prior Publication Data
US 2016/0327461 A1    Nov. 10, 2016

(30) Foreign Application Priority Data
Jan. 29, 2014   (KR) .......................... 10-2014-0011072

(51) Int. Cl.
*B01D 5/00* (2006.01)
*G01N 1/42* (2006.01)
*G01N 1/34* (2006.01)
*G01N 1/40* (2006.01)

(52) U.S. Cl.
CPC ................. *G01N 1/42* (2013.01); *G01N 1/34* (2013.01); *G01N 1/4022* (2013.01); *G01N 2001/4033* (2013.01)

(58) Field of Classification Search
CPC . B01J 2219/00074; B01J 12/007; B01J 8/067
USPC ...................... 422/129, 82.12, 150, 532, 531
See application file for complete search history.

(56) References Cited

U.S. PATENT DOCUMENTS

| 5,307,694 A * | 5/1994 | Nolte ...................... G01N 1/44 73/863.23 |
| 6,578,367 B1 * | 6/2003 | Schaefer ................. F25D 3/102 62/51.1 |

FOREIGN PATENT DOCUMENTS

| JP | 10009452 | 1/1998 |
| JP | 2002236057 | 8/2002 |

* cited by examiner

*Primary Examiner* — Natalia Levkovich
(74) *Attorney, Agent, or Firm* — Cantor Colburn LLP (57) ABSTRACT

Provided is an automatic reduction apparatus for pre-treating a sample for radiocarbon dating, and more particularly, an automatic reduction apparatus for pre-treating a sample for radiocarbon dating capable of preventing peripheral devices of a liquid nitrogen container from being cooled due to scattering of liquid nitrogen supplied to the liquid nitrogen container of a carbon dioxide collector and preventing the peripheral devices from being heated by heat of a reaction furnace at the time of heating the reaction furnace of a reduction reactor.

20 Claims, 11 Drawing Sheets

AUTOMATIC REDUCTION APPARATUS FOR PRE-TREATING SAMPLE FOR RADIOCARBON DATING

TECHNICAL FIELD

The present invention relates to an automatic reduction apparatus for pre-treating a sample for radiocarbon dating, and more particularly, to an automatic reduction apparatus for pre-treating a sample for radiocarbon dating capable of preventing peripheral devices of a liquid nitrogen container from being cooled due to scattering of liquid nitrogen supplied to the liquid nitrogen container of a carbon dioxide collector and preventing the peripheral devices from being heated by heat of a reaction furnace at the time of heating the reaction furnace of a reduction reactor.

BACKGROUND ART

A radiocarbon dating method which has been used to measure the age of remains having an archeological value means a radiocarbon dating method using a principle of collapsing in-vivo radiocarbon after the death of an organism at a constant ratio.

Three kinds of carbon isotopes such as $^{12}C$, $^{13}C$, and $^{14}C$ are mainly present in nature. Here, $^{12}C$ occupies 98.89% of nature, $^{13}C$ occupies 1.11% of nature, and a trace of $^{14}C$ is present in nature. Meanwhile, even though carbon is absorbed into a body of an organism by photosynthesis or breathing, the ratio of $^{12}C$, $^{13}C$, and $^{14}C$ keeps unchanged.

However, after the organism is dead, $^{14}C$ which is instable radiocarbon collapses at a constant rate and thus is changed to $^{14}N$. In this case, the organism suffers from a half-life in which an amount of 14 C is reduced half. The age of the organism may be estimated by the fact that the half-life is about 5,730 years.

To measure the age of a sample such as remains by an accelerator mass spectrometry which is one of the radiocarbon dating methods, there is a need to first extract carbon from the sample. This is referred to as a sample pre-treatment process, which generally includes a chemical pre-treatment process, a vacuum combustion process, and a reduction process.

The chemical pre-treatment process is a process of removing impurities from a sample to be analyzed to prevent errors due to pollutants during an analysis process and removes impurities contained in the sample by known cleaning process, chemical treatment process, drying process, and the like to increases analysis reliability.

The vacuum combustion process means a process of combusting a pre-treated sample under the vacuum to obtain carbon dioxide. High-purity oxygen is emitted from a copper oxide (CuO) powder by putting the pre-treated sample, the copper oxide powder, and an Ag wire in a quartz pipe, sealing the quartz pipe using a torch in a vacuum state, putting the sealed quartz pipe in a muffle furnace, and then combusting the quartz pipe at about 850° C. for 2 hours. In this case, the oxygen oxidizes carbon of an original sample at high temperature to generate carbon dioxide. Further, the Ag wire suppresses and precipitates a generation of sulfur which is a by-product of the combustion.

The carbon dioxide which is generated during the foregoing processes passes through a cooling drier in which dry ice and alcohol are mixed several times and then only the carbon dioxide is solidified, separated, and extracted using the liquid nitrogen.

The reduction process means a process of putting mixed gas of carbon dioxide and hydrogen and an iron powder catalyst in a sealed container and then heating them to extract graphite, which is a carbon powder, by a reaction of $CO_2+2H_2 \rightarrow C+2H_2O$.

The related art manually performs the foregoing graphitization process on each sample. That is, the vacuum combustion process puts the sample, the copper oxide, and the Ag wire in a vacuum pipe, seals the vacuum pipe using the torch in the vacuum state, and then combusts the vacuum pipe and the graphitization process puts the combusted quartz pipe in a flexible bellows of a dry line and breaks the combusted quartz pipe and then sequentially passes the quartz pipe through a liquid nitrogen (LN2)/alcohol trap and an LN2 trap to solidify only pure carbon dioxide ($CO_2$) and collect the solidified carbon dioxide in a carbon dioxide storage tank.

However, the existing method individually performs two steps of the vacuum combustion process and the reduction process on each sample, and as a result, is complicated, has pollution possibility during the processes, and requires much time to perform an operation. Further, when gas in addition to carbon dioxide is mixed due to foreign materials mixed in the sample, it is difficult to confirm and remove the gas. In particular, when gas sulfide is mixed, the reduction reaction itself rarely happens.

To solve the above problem, Patent entitled "Graphitization Apparatus And Graphitization Method Using The Same" (Korean Patent No. 10-0998227) registered on Nov. 29, 2010 is issued to the present applicant.

Figure 1:
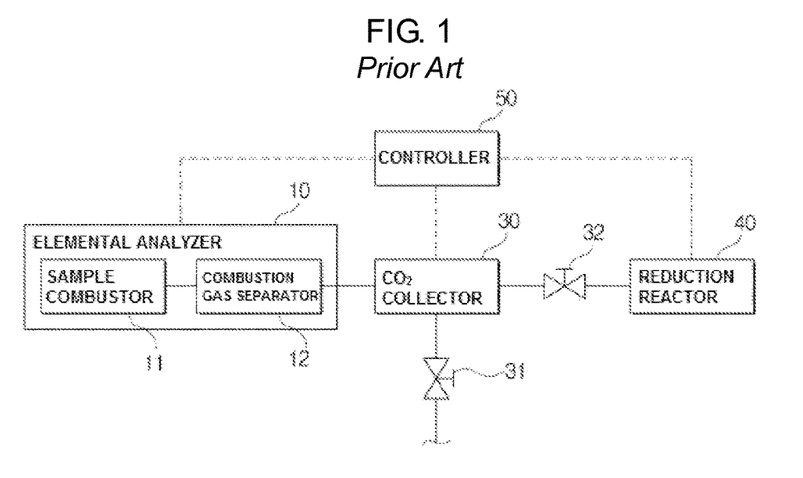
FIG. 1 is a schematic block diagram of a typical automatic reduction apparatus.

According to the above Patent, as illustrated in FIG. 1, the graphitization apparatus includes an elemental analyzer 10 configured to include a sample combustor 11 which combusts a sample and a combustion gas separator 12 which primarily removes impurities included in combustion gas generated from the sample combustor 11 using a gas chromatographic method, a carbon dioxide collector 30 configured to choose and collect only carbon dioxide from the combustion gas passing through the elemental analyzer 10, a reduction reactor 40 configured to reduce the carbon dioxide collected through the carbon dioxide collector 30 to graphite, and a controller 50 configured to control operations of the elemental analyzer 10, the carbon dioxide collector 30, and the reduction reactor 40.

By the above configuration, it is possible to maximally suppress mixing possibility of impurity by primarily removing impurities included in combustion gas of an organic matter using the gas chromatographic function of the elemental analyzer (EA) and then collecting carbon dioxide, to suppress an isotope fractionation effect by remarkably promoting a ratio at which the carbon dioxide is graphitized by optimizing a reaction condition of the graphitization process, to remarkably reduce time required for reaction by optimizing a ration of a reaction container, and to obtain sufficient graphite required for carbon dating only by using a minimum amount of sample.

DISCLOSURE

Technical Problem

An object of the present invention is to provide an automatic reduction apparatus for pre-treating a sample for radiocarbon dating which has an anti-scattering sponge provided in a liquid nitrogen container for preventing liquid nitrogen supplied to the liquid nitrogen container from scattering and a screen for blocking heat exchange between the liquid nitrogen container and peripheral devices thereof.

Another object of the present invention is to provide an automatic reduction apparatus for pre-treating a sample for radiocarbon dating which includes a heat blocking curtain for blocking heat exchange between a reaction furnace heating carbon dioxide and a cooling tank cooling the carbon dioxide at the time of a reduction reaction of carbon dioxide.

Still another object of the present invention is to provide an automatic reduction apparatus which includes a thermocouple measurement device capable of safely inserting a thermocouple into a reaction furnace in horizontal direction and accurately measuring a surface temperature of an object to be measured included in the reaction furnace at all times under a constant condition, simply and easily fixing the thermocouple by a rotatably detachable scheme, not by a typical scheme for attaching the thermocouple using a welding or a bolt, and measuring the surface temperature of the object to be measured using pressurization.

Technical Solution

In one general aspect, an automatic reduction apparatus for pre-treating a sample for radiocarbon dating includes: a carbon dioxide collector configured to choose and collect only carbon dioxide from combustion gas to extract and graphitize carbon within an organic sample and a reduction reactor configured to reduce the carbon dioxide collected by the carbon dioxide collector to graphite, wherein the carbon dioxide collector includes: a carbon dioxide trap configured to solidify the combustion gas; a liquid nitrogen container configured to cool the carbon dioxide trap; a liquid nitrogen injector configured to inject liquid nitrogen into the liquid nitrogen container; and an anti-scattering member configured to be provided in the liquid nitrogen container and adjacently disposed to the liquid nitrogen injector.

The anti-scattering member may be made of a porous material which absorbs and then discharges the liquid nitrogen supplied from the liquid nitrogen injector to suppress the liquid nitrogen from scattering and the anti-scattering member may be a sponge having a void of 1 to 4 mm.

The anti-scattering member may have a bobbin shape in which a few strands of yarns are agglomerated.

The carbon dioxide collector may include a screen configured to be provided in the carbon dioxide trap to seal an opened surface of the liquid nitrogen container when the carbon dioxide trap is received in the liquid nitrogen container.

The carbon dioxide trap may be provided in plural, being spaced apart from each other by a predetermined distance and the screen may be provided in plural to be fitted in each of the carbon dioxide traps and have a plate shape in which a center of the screen is provided with an insertion hole having a diameter corresponding to that of the carbon dioxide trap.

The carbon dioxide collector may include a cooling gas discharger configured to be adjacently disposed to the liquid nitrogen container to suck cooling gas generated from the liquid nitrogen container and discharge the sucked cooling gas to the outside.

The cooling gas discharger may be disposed just above the anti-scattering member.

The reduction reactor may include: a reaction container configured to generate reduction reaction of the carbon dioxide supplied from the carbon dioxide trap; a reacting furnace configured to supply heat to the reaction container; a cooling tank configured to cool the carbon dioxide trap to remove water generated at the time of the reduction reaction; a pressure controller configured to control a pressure inside the reduction reactor; and a heat blocking curtain configured to block heat exchange between the reaction furnace and the reaction container and among the carbon dioxide trap, the cooling tank, and the pressure controller.

The cooling gas discharger may be disposed in an area in which the liquid nitrogen container and the cooling tank which are partitioned by the heat blocking curtain are disposed so as to suck cooling gas generated from the liquid nitrogen container or the cooling tank and discharge the cooling gas to the outside.

The heat blocking curtain may have one end hinged with the reduction reactor so as to be opened and closed.

The automatic reduction apparatus may further include: a thermocouple fixture, wherein the thermocouple fixture includes: a fixing member configured to have a hollow into which a thermocouple is inserted and be attached to an outer side of the reaction furnace and provided with protrusions protruding outwardly, facing each other; a connector configured to have an internal space connected to the thermocouple and to be fastened with the fixing member by a rotatably detachable scheme so that the thermocouple is inserted and fixed into the reaction furnace; and a pressing member configured to be provided with an elastic member pressing the thermocouple in the insertion direction.

The connector may include: a thermocouple fixing part configured to be made of metal having a high heat transfer rate, be formed in a cylindrical shape in which one side of the thermocouple fixing part is opened and the thermocouple fixing part has a hollow, and have an outer side provided with a fastening groove; and a rotating member configured to be formed in a cylindrical shape having a hollow to enclose a predetermined portion of the thermocouple fixing part and have an inner side provided with a protruding part which is fastened with the fastening groove of the thermocouple fixing part.

The rotating member may have an outer side provided with an insulating hole cut in a 'L'-letter shape or a diagonal direction so as to be fastened with a protrusion of the fixing member.

The rotating member may rotate in a 'L'-letter pattern to be detached from the fixing member.

The fixing member may be provided with a through hole through which the thermocouple penetrates.

Advantageous Effects

According to the automatic reduction apparatus for pre-treating a sample for radiocarbon dating in accordance with the exemplary embodiments of the present invention configured as described above, it is possible to prevent the peripheral devices from being cooled due to the liquid nitrogen by preventing the scattering of the liquid nitrogen supplied to the liquid nitrogen container. In particular, it is possible to prevent the sealing force of the sealing member from reducing as the sealing member which is one of the peripheral devices is cooled.

Further, it is possible to improve the heating efficiency of the reaction furnace and the cooling efficiency of the cooling tank by blocking the heat exchange between the reaction furnace and the cooling tank in the reduction reactor.

In addition, it is possible to accurately measure the surface temperature of the object to be measured which is included in the reaction furnace by safely inserting the thermocouple into the reaction furnace in the horizontal direction by the foregoing thermocouple fixture.

DESCRIPTION OF REFERENCE NUMERALS

100: Thermocouple fixture
110: Fixing member
120: Connector
122: Thermocouple fixing part
121a: Insulating hole
122a: Fastening groove
123: Rotating member
123a: Protruding part
130: Pressing member
131: Support plate
132: Elastic member
200: Thermocouple
300: Carbon dioxide collector
310: First valve
320: Second valve
330: Carbon dioxide trap
340: Liquid nitrogen container
341: Liquid nitrogen injector
350: Anti-scattering member
360: Screen
370: Cooling gas discharger
400: Reduction reactor
410: Reaction furnace
420: Reaction container
440: Cooling tank
450: Pressure controller
460: Heat blocking curtain
500: Controller
600: Elemental analyzer
610: Sample combustor
620: Combustion gas separator

BEST MODE

The typical graphitization apparatus as described above has the liquid nitrogen container, which cools the sample gas to collect the carbon dioxide, provided in the carbon dioxide collector, in which since the liquid nitrogen supplied to the liquid nitrogen container is a low temperature of −200° C. or less, the liquid nitrogen is supplied at a high pressure at the time of being supplied to the liquid nitrogen container. In this case, the liquid nitrogen supplied at the high pressure is scattered within the liquid nitrogen container to cool the peripheral devices of the liquid nitrogen container, for example, the sealing member for sealing, thereby reducing the sealing force of the sealing member as the elastic force of the sealing member is lost.

Further, the reduction reactor includes the reaction furnace supplying heat required for the reduction reaction of the carbon dioxide and the cooling tank cooling the carbon dioxide to remove water generated at the time of the reduction reaction of the carbon dioxide, in which since the reaction furnace is heated at high temperature and the cooling tank is cooled at low temperature, the heating efficiency of the reaction furnace and the cooling efficiency of the cooling tank may be reduced due to the heat exchange between the reaction furnace and the cooling tank.

Therefore, an automatic reduction apparatus according to an exemplary embodiment of the present invention is devised to improve the above phenomenon. Hereinafter, the automatic reduction apparatus according to the exemplary embodiment of the present invention as described above will be described in detail with reference to the accompanying drawings.

Figure 2:
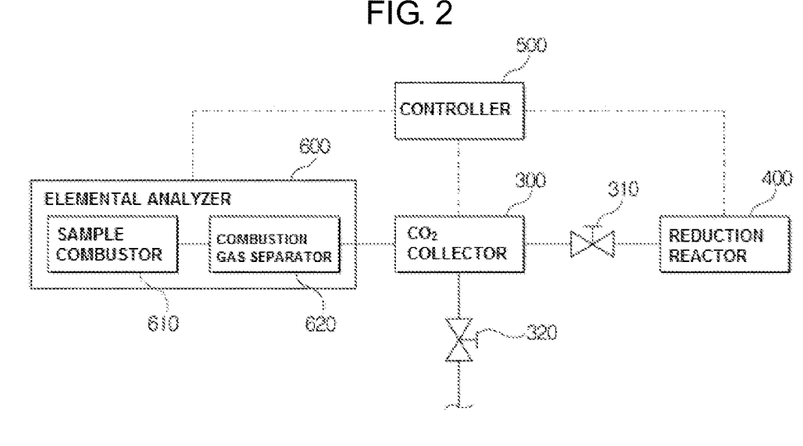
FIG. 2 is a schematic block diagram of an automatic reduction apparatus according to an exemplary embodiment of the present invention.

FIG. 2 is a schematic block diagram of an automatic reduction apparatus according to an exemplary embodiment of the present invention. As illustrated in FIG. 2, the automatic reduction apparatus includes an elemental analyzer 600 configured to include a sample combustor 610 which combusts an extracted sample and a combustion gas separator 620 which primarily removes impurities included in combustion gas generated from the sample combustor 610, a carbon dioxide collector 300 configured to collect only carbon dioxide from gas passing through the elemental analyzer 600, a reduction reactor 400 configured to reduce the carbon dioxide collected through the carbon dioxide collector 300 to graphite, and a controller 500 configured to control the elemental analyzer 600, the carbon dioxide collector 300, and the reduction reactor 400, control reaction temperature, pressure, and a mixed ratio of hydrogen gas, and record a reaction process.

The elemental analyzer 600 is configured to include the sample combustor 610 and the combustion gas separator 620, in which the sample combustor 610 blows high-purity oxygen into a quartz pipe which makes high-purity helium carrier gas flow thereinto and is heated at about 900° C., along with a sample enclosed with a tin foil to combust the sample to be used for carbon dating. The temperature instantly rises up to 1,500° C. due to a fierce exothermic reaction at the time of the combustion of the sample. The combustion gas generated from the sample combustor 610 is supplied to the combustion gas separator 620 which is connected to the sample combustor 610 to primarily remove the impurities included in the combustion gas. The combustion gas separator 620 removes the impurities included in the combustion gas supplied from the sample combustor 610 using a gas chromatography method to primarily separate the carbon dioxide. The carbon dioxide separated by the combustion gas separator 620 includes an extremely small amount of impurities such as nitrogen and hydrogen, including oxygen injected to combust helium which is a carrier gas, and carbon dioxide gas including the helium, the oxygen, and an extremely small amount of other impurities is transferred to the carbon dioxide collector 300.

The carbon dioxide collector 300 is an apparatus which is connected to the elemental analyzer 600 to collect only carbon dioxide from the carbon dioxide gas including the helium, the oxygen, and an extremely small amount of other impurities which are supplied from the elemental analyzer 600.

Figure 3:
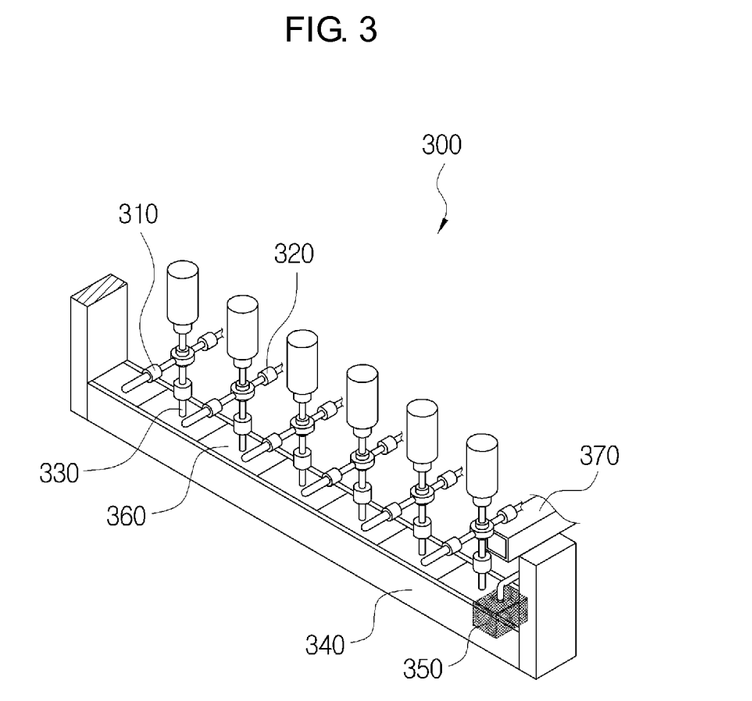
FIG. 3 is a schematic perspective view of a carbon dioxide collector according to an exemplary embodiment of the present invention.
Figure 4:
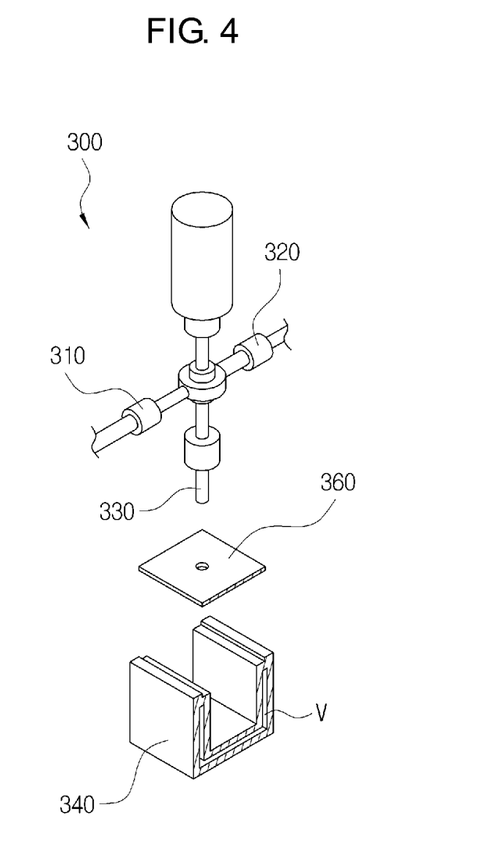
FIG. 4 is a partial perspective view of the carbon dioxide collector.
Figure 5:
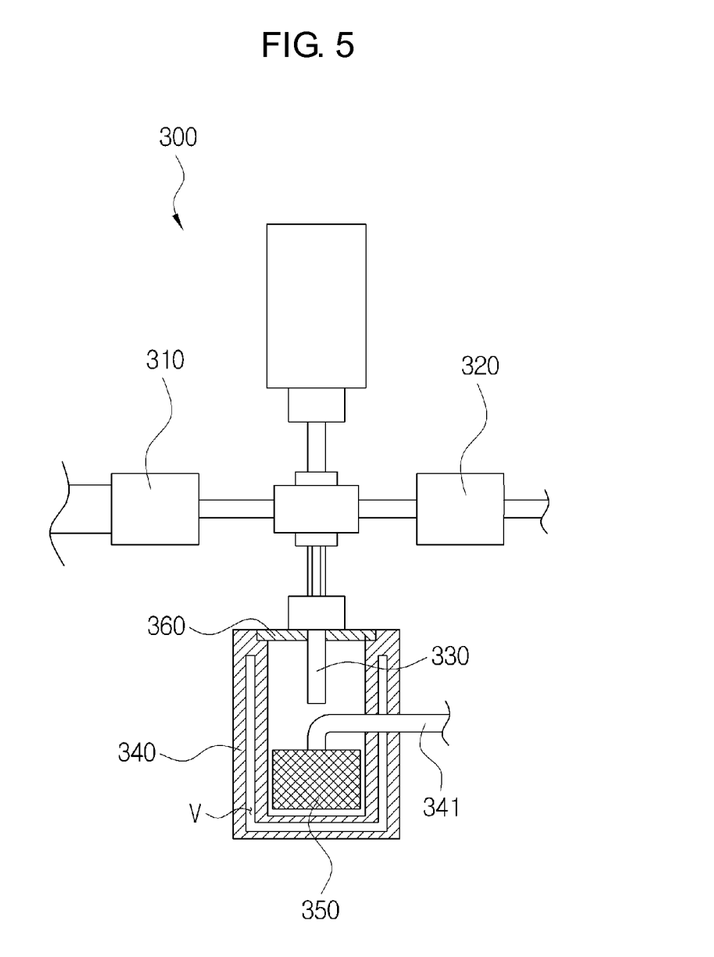
FIG. 5 is a partial cross-sectional view of the carbon dioxide collector.

FIG. 3 is a schematic perspective view of the carbon dioxide collector 300 according to the exemplary embodiment of the present invention, FIG. 4 is a partial perspective view of the carbon dioxide collector 300 according to the exemplary embodiment of the present invention, and FIG. 5 is a partial cross-sectional view of the carbon dioxide collector 300 according to the exemplary embodiment of the present invention.

As illustrated, the carbon dioxide collector 300 includes a carbon dioxide trap 330 configured to solidify the carbon dioxide, a liquid nitrogen container 340 configured to cool the temperature of the carbon dioxide trap 330, a first valve 310 configured to supply the collected carbon dioxide to the reduction reactor, and a second valve 320 configured to discharge the helium, the oxygen, and an extremely small amount of impurities such as nitrogen and hydrogen which are separated from the carbon dioxide and passes the carbon dioxide, which is supplied through the elemental analyzer 600 (see FIG. 2), through the carbon dioxide trap 330 which is dipped in the liquid nitrogen container 340 to make the carbon dioxide into a solid state and then removes the helium, the oxygen, and an extremely small amount of other remaining gases using a vaporization temperature difference, thereby obtaining high-purity carbon dioxide. In this case, the vaporized helium, oxygen, and other remaining gases are discharged to the outside through the second valve 320. The carbon dioxide collected by the carbon dioxide collector 300 is supplied to the reduction reactor 400 through the first valve 310 for graphitization reaction. The liquid nitrogen container 340 is made of quartz in a double pipe form to insulate the liquid nitrogen filled in inner thereof, in which an inside of the double pipe may be formed in vacuum (V). The reason of applying the quartz to the liquid nitrogen container 340 is that the liquid nitrogen container may be easily molded without being deformed and damaged even when storing the liquid nitrogen having a temperature of −200° C. or less.

In this case, the liquid nitrogen is supplied to the liquid nitrogen container 340 through a liquid nitrogen injector 341 so that the liquid nitrogen container 340 receives a constant level of liquid nitrogen. The liquid nitrogen container 340 is configured to be relatively elevated with respect to the carbon dioxide trap 330. Therefore, the liquid nitrogen container 340 may have the carbon dioxide trap 330 selectively received or separated therein or therefrom. For example, the carbon dioxide trap 330 is received in the liquid nitrogen container 340 by the elevation of the liquid nitrogen container 340 and the carbon dioxide trap 330 is separated from the liquid nitrogen container 340 by the falling of the liquid nitrogen container 340.

Further, at the time of the reduction reaction to be described below, the carbon dioxide trap 330 is received in the cooling tank 440 (see FIGS. 8 and 9) to remove water generated at the time of the reduction reaction.

The liquid nitrogen supplied from the liquid nitrogen injector 341 is a low temperature of about −200° C. and therefore is supplied at high pressure. Here, the automatic reduction apparatus according to the exemplary embodiment of the present invention for preventing the liquid nitrogen supplied at high pressure from scattering has the following configuration. An anti-scattering member 350 may be provided within the liquid nitrogen container 340. The anti-scattering member 350 is configured to prevent the high-pressure liquid nitrogen supplied from the liquid nitrogen injector 341 from scattering and may be formed of a porous material. As an example of the porous material, a sponge or a bobbin in which a few strands of yarns are agglomerated to form a void may be applied.

The porous material has the liquid nitrogen discharged from the liquid nitrogen injector 341 and absorbed into the void therein and leaks the liquid nitrogen into the liquid nitrogen container 340, and therefore mitigates a shock when the liquid nitrogen is introduced into the liquid nitrogen container 340 at a high pressure to effectively suppress the liquid nitrogen from bounding or scattering to the outside of the liquid nitrogen container 340.

The void of the porous material may be 1 to 4 mm. The reason is that when the void is less than 1 mm, the supply of the liquid nitrogen is not smooth and when the void exceeds 4 mm, the anti-scattering effect of the liquid nitrogen is reduced.

Further, the liquid nitrogen container 340 is provided with a screen 360 to prevent the chill from being transferred to an upper end of the carbon dioxide trap 330. The screen 360 has a plate shape in which a center thereof is provided with a fitting hole and the carbon dioxide trap 330 may be fitted and fixed in the fitting hole. Therefore, a diameter of the fitting hole is formed to be equal to that of the carbon dioxide trap 330. The screen 360 is configured to seal an opened surface of the liquid nitrogen container 340 when the carbon dioxide trap 330 is received in the liquid nitrogen container 340. When the carbon dioxide trap 330 is provided in plural, the screen 360 may be provided in plural to be fitted in each of the carbon dioxide traps 330. When the single screen having the plurality of fitting holes is applied to the plurality of carbon dioxide traps 330, the fitting holes in which each of the carbon dioxide traps 330 is fitted are accurately machined and therefore may not be easily manufactured, and when an interval between the fitting holes is not accurately machined, the fitting holes are press-fitted thereinto and thus a load of the screen 360 is applied to the carbon dioxide trap 330, such that the carbon dioxide trap 330 may be damaged. The screen 360 may be made of a general rubber material. As the rubber material, for example, a urethane material may be used.

Further, when the single screen is applied, an unnecessary load may also be applied to the carbon dioxide trap 330 due to a thermal expansion of the screen 360.

The screen 360 as described above seals the opened surface of the upper portion of the liquid nitrogen container 340 when receiving the carbon dioxide trap 330 depending on the rising of the liquid nitrogen container 340. Therefore, it is possible to prevent the liquid nitrogen in the liquid nitrogen container 340 from being leaked to the outside of the liquid nitrogen container 340.

Further, the carbon dioxide collector 300 may be further provided with a cooling gas discharger 370 for discharging cooling gas generated from the liquid nitrogen container 340 to the outside. The cooling gas discharger 370 may be configured to generally include a duct and a fan for circulating gas and prevent the peripheral devices of the liquid nitrogen container 340 from being cooled due to the cooling gas through the cooling gas discharger 370. In particular, the duct of the cooling gas discharger 370 may be disposed over the anti-scattering member 350 which is positioned at a liquid nitrogen injector 341. The reason is that the scattering or leaking of the liquid nitrogen from the liquid nitrogen injector 341 may frequently occur.

Figure 6:
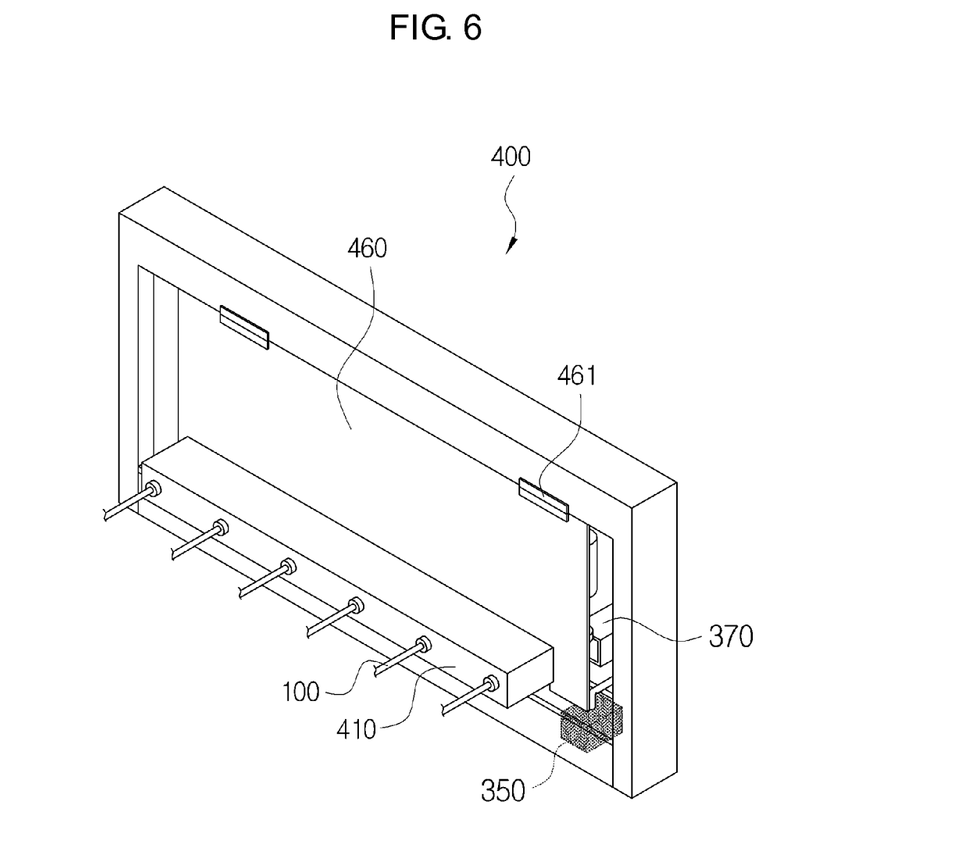
FIG. 6 is a schematic perspective view of a reduction reactor according to an exemplary embodiment of the present invention (at the time of coupling a reaction furnace).
Figure 7:
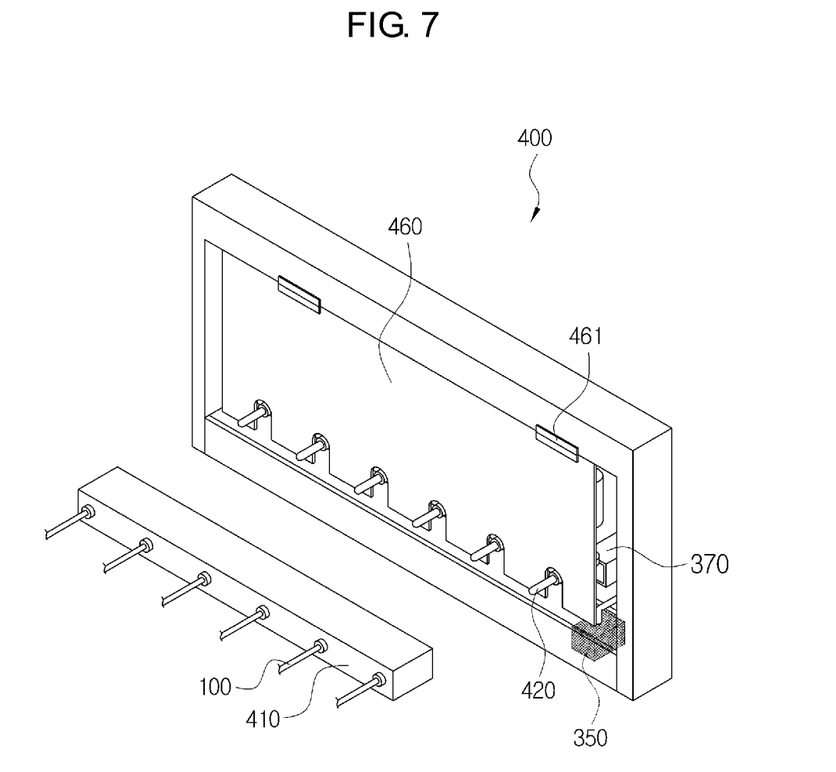
FIG. 7 is another schematic perspective view of the reduction reactor (at the time of separating the reaction furnace).
Figure 8:
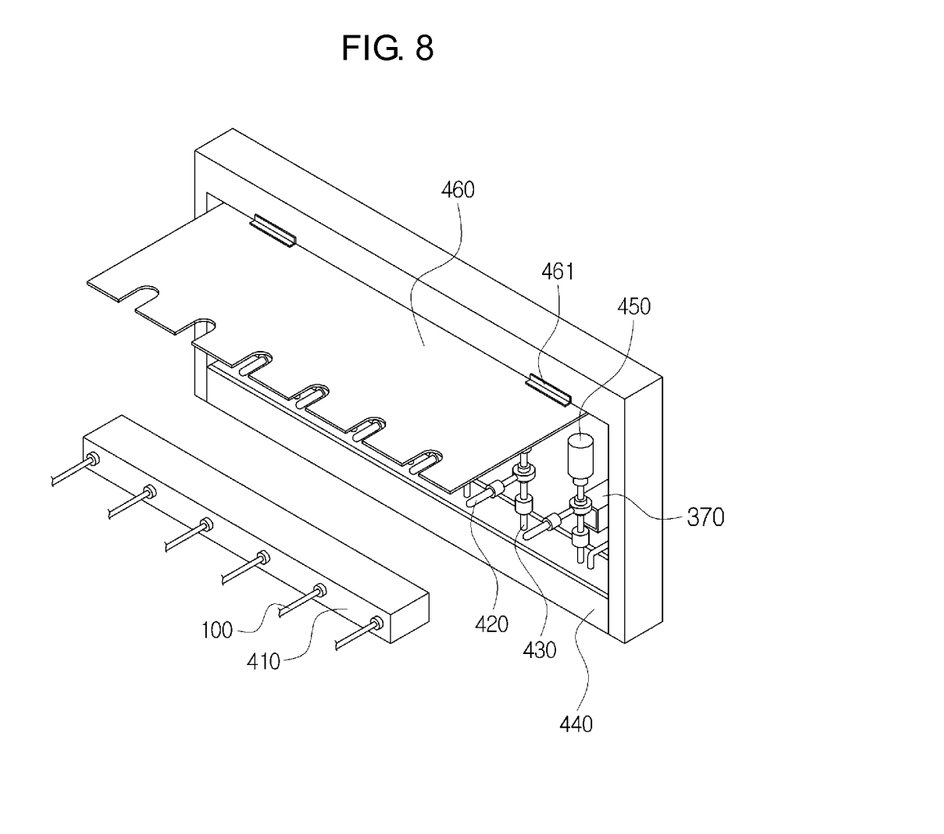
FIG. 8 is still another schematic perspective view of the reduction reactor (at the time of opening a heat blocking curtain).
Figure 9:
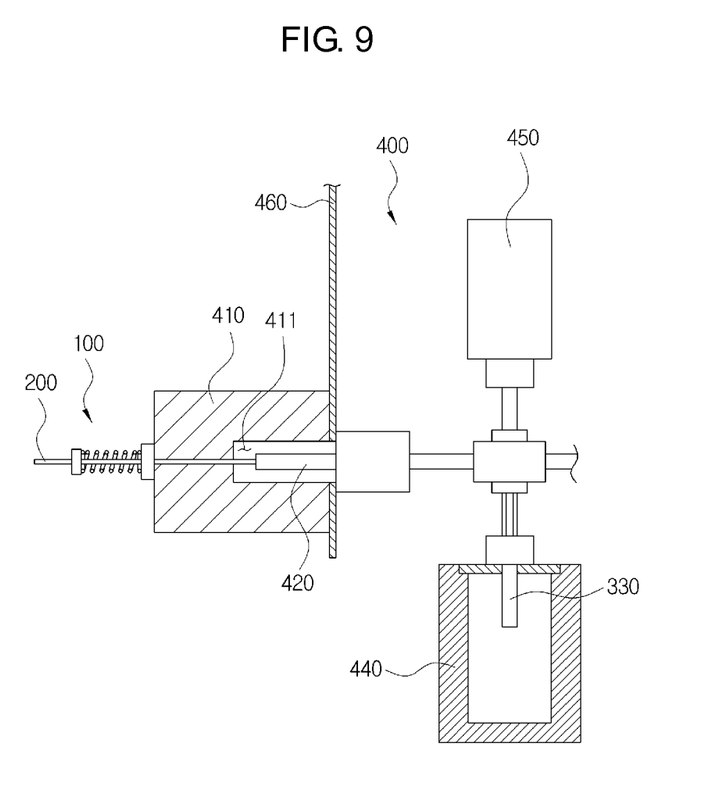
FIG. 9 is a partial perspective view of the reduction reactor.

FIG. 6 is a schematic perspective view of a reduction reactor 400 according to an exemplary embodiment of the present invention at the time of coupling a reaction furnace 410, FIG. 7 is a schematic perspective view of the reduction reactor 400 at the time of separating the reaction furnace 410, and FIG. 8 is a schematic perspective view of the reduction reactor 400 at the time of opening a heat blocking curtain 460. Further, FIG. 9 is a partial perspective view of the reduction reactor 400.

As illustrated, the reduction reactor 400 includes the reaction furnace 410 configured to supply heat required for reaction, a reaction container 420 in which a carbon reduction reaction happens, the carbon dioxide trap 330 configured to be connected to the reaction container 420 to remove water generated at the time of the reduction reaction, the cooling tank 440 configured to cool the temperature of the carbon dioxide trap 330 to about −50° C., and a pressure controller 450 configured to make the inside of the reduction reactor 400 into a vacuum state and measure a pressure therein. A thermocouple 200 for measuring the temperature of the reaction container 420 and a thermocouple fixture 100 fixing the thermocouple 200 are provided on the reaction furnace 410 and a configuration of the thermocouple 200 and the thermocouple fixture 100 will be described below. The cooling tank 440 is configured to be relatively elevated with respect to the carbon dioxide trap 330. Therefore, the cooling tank 440 may have the carbon dioxide trap 330 selectively received or separated therein or therefrom, similar to the liquid nitrogen container 340 as described above. For example, the carbon dioxide trap 330 is received in the cooling tank 440 by the elevation of the cooling tank 440 and the carbon dioxide trap 330 is separated from the cooling tank 440 by the falling of the cooling tank 440.

That is, the carbon dioxide trap 330 is received in the liquid nitrogen container 340 at the time of collecting the carbon dioxide and the liquid nitrogen container 340 and the cooling tank 440 are switched at the time of the reduction reaction and thus the carbon dioxide trap 330 may be received in the cooling tank 440.

The reaction furnace 410 supplies heat required for the carbon reduction reaction and a body thereof is made of a metal material having excellent thermal conductivity such as a silver ingot and is provided with a receiving groove 411 in which the reaction container 420 may be received and a specific portion of the reaction furnace 410 is provided with a hot wire (not illustrated). As the reaction container 420, a quartz pipe which is a space in which the carbon reduction reaction happens is used.

In this case, the automatic reduction apparatus according to the exemplary embodiment of the present invention may be provided with a heat blocking curtain 460 to prevent heat generated from the reaction furnace 410 from being transferred to the carbon dioxide trap 330, the cooling tank 440, and the pressure controller 450. The heat blocking curtain 460 is disposed between the reaction furnace 410 and the reaction container 420 and among the carbon dioxide trap 330, the cooling tank 440, and the pressure controller 450 and may be provided with a through groove as much as the number of reaction containers 420 so as to make the reaction container 420 penetrate therethrough. Further, the heat blocking curtain 460 may be coupled with the reduction reactor 400 by a hinge coupling means 461 so as to be opened and closed. The heat blocking curtain 460 is configured to be opened and closed and is configured to facilitate the maintenance of the carbon dioxide trap 330, the cooling tank 440, and the pressure controller 450. Further, the foregoing cooling gas discharger 370 is disposed in an internal space of the heat blocking curtain 460 to prevent the low-temperature nitrogen gas leaked from the liquid nitrogen container 340 from being leaked to the outside of the heat blocking curtain 460. In particular, the cooling gas discharger 370 does not affect the high-temperature reaction container 420.

Hereinafter, the thermocouple fixture 100 according to the exemplary embodiment of the present invention will be described in more detail with reference to the drawings.

Figure 10:
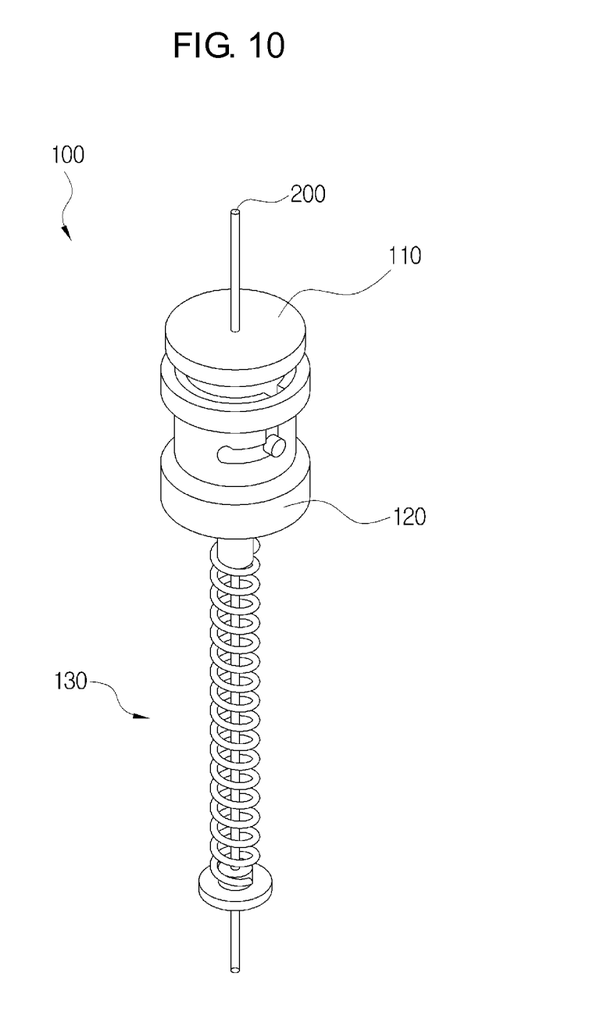
FIG. 10 is a schematic perspective view of a thermocouple fixture according to an exemplary embodiment of the present invention.
Figure 11:
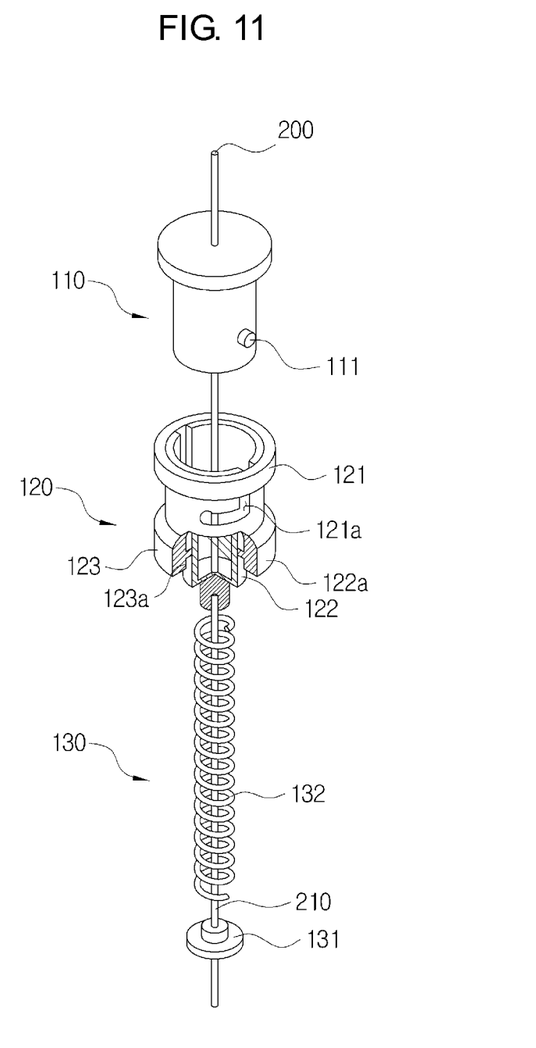
FIG. 11 is an exploded perspective view of the thermocouple fixture.
Figure 12:
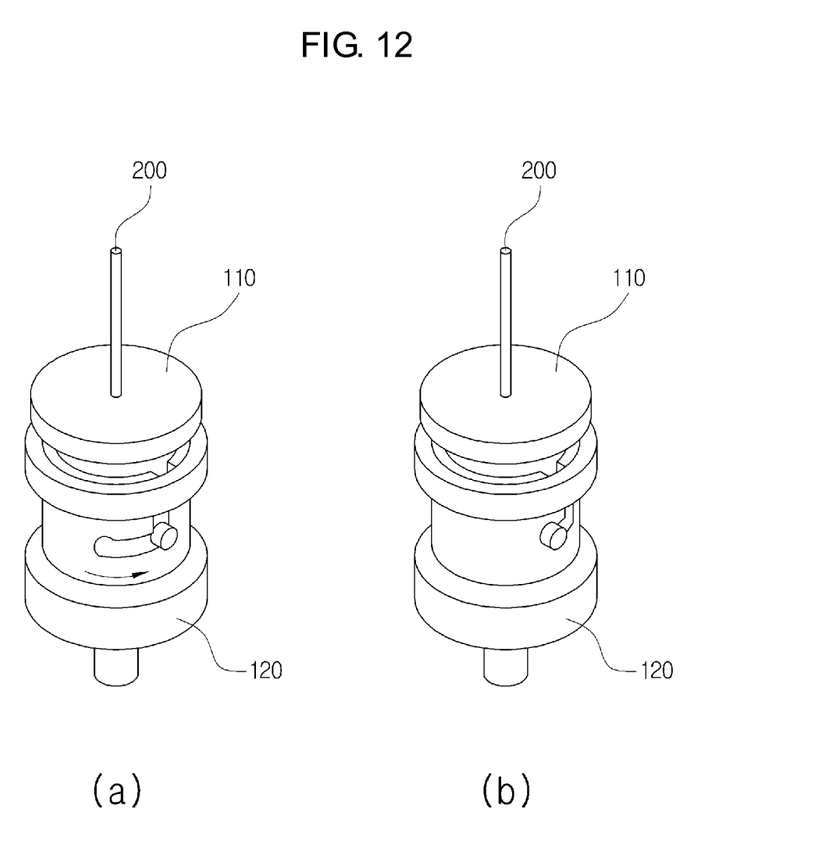
FIG. 12 is a flow chart exemplarily illustrating a process of fastening a rotating member and a fixing member of the thermocouple fixture.

FIG. 10 is a schematic perspective view of the thermocouple fixture 100 according to an exemplary embodiment of the present invention and FIG. 11 is an exploded perspective view of the thermocouple fixture 100. Further, FIG. 12 is a flow chart exemplarily illustrating a process of fastening a rotating member 123 of the thermocouple fixture 100 with a fixing member 110.

As illustrated in FIGS. 10 and 11, the thermocouple fixture 100 according to the exemplary embodiment of the present invention includes the fixing member 110, a connector 120, and a pressing member 130.

The fixing member 110 is attached on an outer side of the foregoing reaction furnace 410 (see FIG. 8) and provided with protrusions 111 protruding outwardly, facing each other.

The connector 120 has the thermocouple 200 connected to an internal space thereof and the thermocouple 200 is fastened with the fixing member 110 so that it is inserted into the receiving groove 411 (see FIG. 9) of the reaction furnace 410 in a horizontal direction to be fixed.

In more detail, the connector 120 includes a thermocouple fixing part 122 and the rotating member 123.

The thermocouple fixing part 122 is made of metal having a high heat transfer coefficient and is formed in a cylindrical shape in which one side of the thermocouple fixing part 122 is opened and the thermocouple fixing part 122 has a hollow and a center inside the thermocouple fixing part 122 is connected to the thermocouple 200 by a welding.

The other end of the thermocouple fixing part 122 is connected to a thermoelement wire so that the thermocouple fixing part 122 serves to fix the thermocouple 200 while serving as a medium which transfers heat transferred from the thermocouple 200 to the thermo element wire. For reference, the thermoelement wire may be connected to a heat measurer (not illustrated).

Further, an outer side of the thermocouple fixing part 122 may be provided with a fastening groove 122a. The fastening groove 122a is fastened with a protruding part 123a of the rotating member 123.

The rotating member 123 is formed in a cylindrical shape having a hollow, enclosing a predetermined portion of the thermocouple fixing part 122 and an inner side thereof is provided with the protruding part 123a which is fastened with the fastening groove 122a of the thermocouple fixing part 122.

Further, an outer side of the rotating member 123 is provided with an insulating groove 121a having the protrusion 111 of the fixing member 110 inserted and fixed thereinto.

In more detail, the insulating groove 121a is formed on the outer side of the rotating member 123 to have a 'L' direction and one of both ends of the insulating groove 121a has the protruding part inserted thereinto and the other one thereof is fixedly provided with the protrusion 111 inserted into the insulating groove 121a.

Therefore, referring to (a) of FIG. 12, the rotating member 123 has the protrusion 111 inserted thereinto and then rotates to be fastened and the rotating member 123 rotates in a 'L'-letter pattern to be detached from the fixing member 110.

The pressing member 130 serves to press the thermocouple 200 in a horizontal direction, in more detail, includes a support plate 131 and an elastic member 132.

The support plate 131 is formed in a '⊥'-letter shape in which a center thereof protrudes, in which the protruding portion is inserted into the elastic member 132 and an outer surface of the protruding portion is coupled with one end of the elastic member 132 by a welding or a fastening member.

The elastic member 132 may be a high elastic spring and one end thereof is fixed to the outer surface of the protruding portion and the other end thereof is coupled with the thermocouple fixing part 122 by the welding or the fastening member.

Therefore, the thermocouple fixture 100 according to an exemplary embodiment of the present invention safely inserts the thermocouple 200 into the reaction furnace 410 in a horizontal direction to be able to accurately measure the surface temperature of the reaction container 420 (see FIG. 8) which is included in the reaction furnace 410.

Further, it is possible to conveniently and easily fix the thermocouple by the rotatably detachable scheme, not by the typical scheme for attaching the thermocouple 200 to the reaction furnace 410 by the welding or the bolt.

Further, it is possible to measure different temperatures on the surface of the object to be measured with the pressed thermocouple, by applying a varying pressure to the thermocouple contacting the surface of the object to be measured using the pressing member. That is, it is possible to measure the surface temperature of the object to be measured when the thermocouple contacts the object to be measured at the relatively stronger pressure by applying the pressing member having the high elastic force and measure the surface temperature of the object to be measured when the thermocouple contacts the object to be measured at the relatively weaker pressure by applying the pressing member having a low elastic force.

The present invention should not be construed to being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall in the scope of the present invention.

The invention claimed is:

1. An automatic reduction apparatus for pre-treating a sample for radiocarbon dating, comprising:
   a carbon dioxide collector; and
   a reduction reactor to reduce carbon dioxide collected by the carbon dioxide collector to graphite and fluidically connected to the carbon dioxide collector,
   wherein the reduction reactor comprises
      a reaction container;
      a reacting furnace in which the reaction container is received and configured to supply heat to the reaction container; and
      a heat blocking curtain disposed between the reaction furnace and the reaction container, and a carbon dioxide trap; and
   wherein the carbon dioxide collector includes:
      the carbon dioxide trap to solidify carbon dioxide gas, wherein the carbon dioxide trap is connected to the reaction container;
      a liquid nitrogen container to cool the carbon dioxide trap, wherein the carbon dioxide trap is received in the liquid nitrogen container; and
      a liquid nitrogen injector fluidically connected to the liquid nitrogen container to inject liquid nitrogen into the liquid nitrogen container.

2. The automatic reduction apparatus of claim 1, further comprising a porous material which absorbs and then discharges the liquid nitrogen supplied from the liquid nitrogen injector to suppress the liquid nitrogen from scattering.

3. The automatic reduction apparatus of claim 2, further comprising a sponge having a void of 1 to 4 mm.

4. The automatic reduction apparatus of claim 2, further comprising an anti-scattering member having a bobbin shape in which a few strands of yarns are agglomerated.

5. The automatic reduction apparatus of claim 1, wherein the carbon dioxide collector includes a screen configured to be provided in the carbon dioxide trap to seal an opened surface of the liquid nitrogen container when the carbon dioxide trap is received in the liquid nitrogen container.

6. The automatic reduction apparatus of claim 5, wherein the carbon dioxide trap is provided in plural, being spaced apart from each other by a predetermined distance, and
   the screen is provided in plural to be fitted in each of the carbon dioxide traps and has a plate shape in which a center of the screen is provided with an insertion hole having a diameter corresponding to that of the carbon dioxide trap.

7. The automatic reduction apparatus of claim 2, wherein the carbon dioxide collector includes a cooling gas discharger configured to be adjacently disposed to the liquid nitrogen container to suck cooling gas generated from the liquid nitrogen container and discharge the sucked cooling gas to the outside.

8. The automatic reduction apparatus of claim 7, wherein the cooling gas discharger is disposed just above the anti-scattering member.

9. The automatic reduction apparatus of claim 1, wherein the reduction reactor further includes:
   a cooling tank, wherein the carbon dioxide trap is received in the cooling tank, wherein the cooling tank is configured to cool the carbon dioxide trap; and
   a pressure controller fluidically connected to the reduction reactor and configured to make an inside of the reduction reactor into a vacuum state,
   wherein the heat blocking curtain is disposed between the reaction furnace and the reaction container, and the carbon dioxide trap, the cooling tank, and the pressure controller.

10. The automatic reduction apparatus of claim 9, wherein a cooling gas discharger is disposed in an area in which the liquid nitrogen container and the cooling tank which are partitioned by the heat blocking curtain are disposed so as to suck cooling gas generated from the liquid nitrogen container or the cooling tank and discharge the cooling gas to the outside.

11. The automatic reduction apparatus of claim 9, wherein the heat blocking curtain has one end hinged with the reduction reactor so as to be opened and closed.

12. The automatic reduction apparatus of claim 9, further comprising:
a thermocouple fixture,
wherein the thermocouple fixture includes:
a fixing member including a hollow into which a thermocouple is inserted and attached to an outer side of the reaction furnace and provided with protrusions protruding outwardly, facing each other;
a connector including an internal space connected to the thermocouple and fastened with the fixing member so that the thermocouple is inserted and fixed into the reaction furnace; and
a pressing member with an elastic member pressing the thermocouple.

13. The automatic reduction apparatus of claim 12, wherein the connector includes:
a thermocouple fixing part made of metal having a high heat transfer rate, formed in a cylindrical shape in which the thermocouple fixing part has a hollow, and including an outer side provided with a fastening groove; and
a member formed in a cylindrical shape having a hollow to enclose a predetermined portion of the thermocouple fixing part and including an inner side provided with a protruding part which is fastened with the fastening groove of the thermocouple fixing part.

14. The automatic reduction apparatus of claim 13, wherein:
the member formed in a cylindrical shape having a hollow to enclose a predetermined portion of the thermocouple fixing part has an outer side provided with an insulating hole to be fastened with a protrusion of the fixing member, and
the insulating hole is cut in a 'L'-letter shape.

15. The automatic reduction apparatus of claim 13, wherein the member formed in a cylindrical shape having a hollow to enclose a predetermined portion of the thermocouple fixing part rotates in a 'L'-letter pattern to be detached from the fixing member.

16. The automatic reduction apparatus of claim 12, wherein the fixing member is provided with a through hole through which the thermocouple penetrates.

17. The automatic reduction apparatus of claim 12, further comprising the thermocouple inserted in the fixing member.

18. The automatic reduction apparatus of claim 9, wherein the carbon dioxide trap is connected to the reaction container.

19. The automatic reduction apparatus of claim 1, wherein the carbon dioxide collector is connected to the reduction reactor.

20. The automatic reduction apparatus of claim 1, further comprising:
an elemental analyzer comprising:
a sample combustor; and
a combustion gas separator connected to the sample combustor,
wherein the combustion gas separator is connected to the carbon dioxide collector and provides the carbon dioxide collected by the carbon dioxide collector.

* * * * *